United States Patent [19]
Kluge et al.

[11] 4,436,914
[45] Mar. 13, 1984

[54] BENZODIOXANE-IMIDAZOLINE COMPOUNDS AS ANTIHYPERTENSIVES

[76] Inventors: Arthur F. Kluge; Arthur M. Strosberg; Roger L. Whiting; George A. Christie, all of 3401 Hillview Ave., Palo Alto, Calif. 94304

[21] Appl. No.: 289,679

[22] Filed: Aug. 3, 1981

[51] Int. Cl.³ .................. C07D 405/04; C07D 405/06
[52] U.S. Cl. ............................... 548/348; 424/273 R; 549/366
[58] Field of Search ..................... 548/348; 424/273 R

[56] References Cited

U.S. PATENT DOCUMENTS 2,979,511  4/1961  Krapcho et al. ................... 548/348

FOREIGN PATENT DOCUMENTS 2068376  8/1981  United Kingdom ............... 548/348

OTHER PUBLICATIONS

Hofmann, K., *Imidazole and Its Derivatives*, Part I, Interscience, New York, 1953, p. 217.
Chapleo, C., et al., *Tett. Lett.*, 22(48), 4839 (Nov. 1981).

*Primary Examiner*—Richard A. Schwartz
*Attorney, Agent, or Firm*—Hana H. Dolezalova; Tom Moran

[57] ABSTRACT

Compounds of the formula

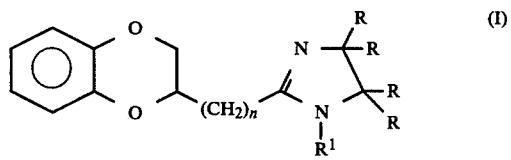

and the pharmaceutically acceptable acid addition salts thereof, wherein:

n is an integer equal to 0, 1, 2 or 3;

$R^1$ is hydrogen, lower alkyl, optionally substituted phenyl or optionally substituted phenyl lower alkyl;

each R is independently hydrogen, lower alkyl, optionally substituted phenyl, or optionally substituted phenyl lower alkyl;

are $\alpha_2$ blockers, and, therefore, are useful in treating essential hypertension and depression, and in inhibiting platelet aggregation.

3 Claims, No Drawings

BENZODIOXANE-IMIDAZOLINE COMPOUNDS AS ANTIHYPERTENSIVES

BACKGROUND OF THE INVENTION

The present invention is concerned with compounds, compositions and methods useful for treating symptomologies in human beings which are affected by $\alpha_2$ blockade. In particular, compounds wherein benzodioxane is linked through 0 to 3 methylene groups to an imidazoline nucleus are thus useful.

Large numbers of compounds are known which affect various physiological systems related to synaptic control. The class most closely related to the compounds of the present invention is that disclosed in U.S. Pat. No. 2,979,511, issued Apr. 11, 1961 to Krapcho, et al. This patent purports to disclose, generically, some of the compounds of the present invention, specifically those wherein n is equal to 0 or 1, the R groups are hydrogen or lower alkyl, and $R^1$ is hydrogen. Also, specifically claimed in the Krapcho patent are 2-(1,4-benzodioxan-2-yl)-imidazoline, and its hydrochloride. These compounds are disclosed as peripherally acting vasolidators. The methods of preparation given therein, do not, in our hands, yield the imidazoline ring, but rather the open chain counterparts.

The present invention concerns a suite of imidazoline compounds, which are attached to benzodioxane moiety through methylene chains varying from 0 to 3 methylene units, and which optionally carry aromatic as well as alkyl substituents.

These compounds have $\alpha_2$ blocking activity.

SUMMARY OF THE INVENTION

In one aspect this invention concerns imidazoline derivatives of the general formula

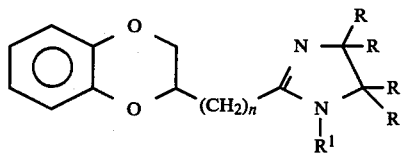

ps and the pharmaceutically acceptable acid addition salts thereof,
wherein:
n is an integer equal to 0, 1, 2 or 3;
$R^1$ is hydrogen, lower alkyl, optionally substituted phenyl, or optionally substituted phenyl lower alkyl;
each R is independently hydrogen, lower alkyl, optionally substituted phenyl, or optionally substituted phenyl lower alkyl.

These compounds have been shown to block $\alpha_2$ receptors in pithed rats, hence in two other aspects the invention concerns a method for affecting physiological phenomena related to $\alpha_2$ control in human beings, using the compounds of formula I, and compositions for this purpose containing these compounds. In a fourth aspect, the invention is directed to methods of preparing these compounds.

DETAILED DESCRIPTION OF THE INVENTION

Definitions as used herein:

"Alkyl" means a branched or unbranched saturated hydrocarbon chain containing 1-6 carbon atoms, such as methyl, ethyl, propyl, tert-butyl, n-hexyl and the like;

"Lower alkyl" means a branched or unbranched saturated hydrocarbon chain of 1-4 carbons, such as, for example, methyl, ethyl, n-propyl, i-butyl and the like.

"Pharmaceutically acceptable acid addition salt" refers to those salts which retain the biological effectiveness and properties of the free bases and which are not biologically or otherwise undesirable, formed with inorganic acids such as hydrochloride acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfuric acid, ethanesulfonic acid, p-toluenesulfonic acid, salicyclic acid and the like.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Substituted phenyl" as used herein means that one or more hydrogens of the phenyl ring are replaced by identical moieties selected from the group consisting of halo, lower alkyl, or trifluoromethyl. In the context of the present invention, said replacement may be at any position of the phenyl ring, and a maximum of 3 hydrogens may be so replaced.

"Optionally substituted phenyl lower alkyl" means a moiety in which the phenyl, which may or may not be substituted as described above, is attached to the nitrogen or 4- or 5-C of the imidazole ring of the compounds of this invention by an intervening lower alkyl. Such embodiments of "optionally substituted phenyl lower alkyl", are, for example benzyl, phenylethyl, 2-(4-fluorophenyl)ethyl 3-(3,5-dimethylphenyl)-n-propyl and the like.

PROCESS FOR PREPARATION OF THE COMPOUNDS OF THE INVENTION

Compounds of the invention are prepared according to Reaction Scheme I.

REACTION SCHEME I

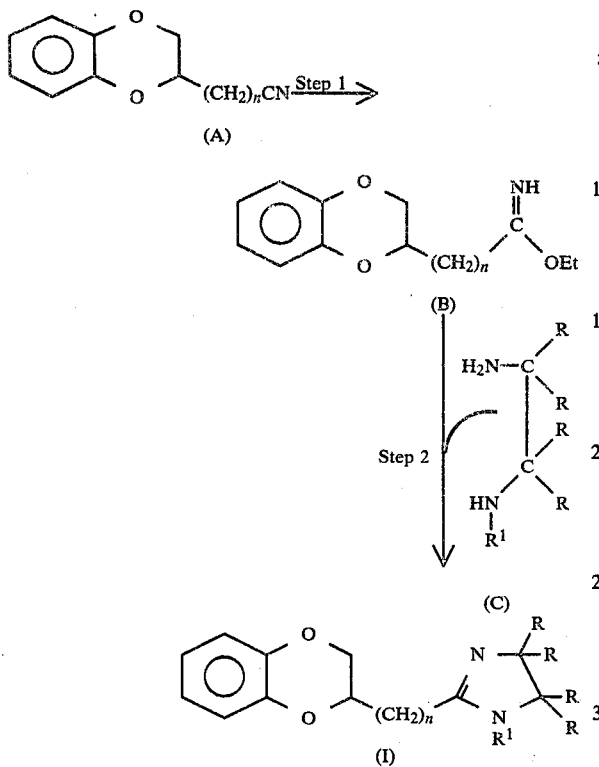

R, $R^1$ and n have their previously defined meanings.

Compounds A, B and I contain at least one chiral center—i.e. the 2-position of the benzodioxane nucleus. Accordingly, the compounds of the present invention may be prepared in either optically active form or as racemic mixtures. Unless otherwise specified, the compounds described herein are all in the racemic form. However, the scope of the subject invention herein is not to be considered limited to the racemic forms, but to encompass the individual optical isomers of the compounds.

If desired, the compounds herein may be resolved into their optical antipodes by conventional resolution means; for example by separation (e.g. fractional crystallization) of the diastereomeric salts formed by the reaction of these compounds with optically active acids. Exemplary of such optically active acids are the optically active forms of camphor-10-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers of the compounds of Formula I.

Compound C may also be chiral if the R groups on a particular carbon are not identical. Hence, the resulting compounds of Formula I would have an additional one or two chiral centers in the imidazoline ring, and would therefore exist in $2^x$ stereoisomeric forms, where x is the total number of chiral centers. Thus, the invention is intended to include isolated individual isomers, racemic mixtures of enantiomers of a single diasteromeric form, and mixtures containing more than one diastereomer. Separation of diastereomers, is, of course, carried out by means standard for separation of chemical compounds in general, such as fractional crystallization and chromatography. Resolution of enantiomers is effected as described hereinabove.

Further, the compounds of formula I, may exist in tautomeric forms when $R^1$ is hydrogen. In that case, both sets of R groups on the saturated bond of the ring are equivalent because the equilibration between the two tautomers does not allow isolation of either alternative. Accordingly, the invention includes both tautomeric forms of such embodiments. However, in those embodiments wherein $R^1$ is not hydrogen, the tautomer is fixed in the position shown. The form which results in the compound of formula I according to the reaction scheme shown, depends on the structure of formula C. The nitrogen containing a non-hydrogen $R^1$ will automatically end up in the imidazoline ring as the saturated nitrogen.

Isolation and purification of the compounds and intermediates described can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The salt products are also isolated by conventional means. For example, the reaction mixtures may be evaporated to a dryness, and the salts can be further purified by conventional methods.

The compounds of formula A, are prepared as described by Augstein, et al in *J. Med. Chem.*, 8: 446 (1965). The compounds of formula C are either commercially available or easily prepared by means known to those in the art.

The conversion of the compound of formula A into the compound of formula B (step 1) is carried out by treating the compound of formula A with an excess of alcohol under acidic conditions at low temperature, in the range of $-10°$ C. to $+10°$ C. and in the absence or presence of an aprotic organic solvent, such as, for example, diethyl ether or tetrahydrofuran. A preferred temperature range is 1° C. to 5° C.; preferred alcohols are methanol, ethanol and isopropanol; a preferred solvent is diethyl ether and a preferred acid is anhydrous hydrochloric acid. This reaction mixture is allowed to stand at the aforementioned low temperature for several hours or days before being warmed to room temperature of 15° to 30°, and the crude product is permitted to percipitate out. The crude product is recovered and purified by conventional means.

In the succeeding condensation of the compound of formula B with the compound of formula C to form the compound of formula I, approximately equilimolar amounts of the two reagents are dissolved in a suitable polar solvent such as, for example, methanol, ethanol, isopropanol, preferably ethanol, and heated to enhance the reaction, to temperatures in the range of room temperature to 100° C., preferably at the reflux temperature of the solvent. The mixture is heated for a period of about 10 minutes to 24 hours, preferably 3 to 4 hours, or until reaction is complete. The product of formula I is then recovered by acidifying the reaction mixture and extracting the hydrochloride salt.

If the compound of formula I is an embodiment wherein $R^1$ is hydrogen, conversion to the alkylated or phenyl lower alkyl ring nitrogen compounds can then be effected as follows:

The compound of formula I or its salt is dissolved in an aprotic organic solvent, such as, for example, dimethoxyethane, dimethylformamide (DMF) or acetonitrile, preferably DMF and an excess of alkaline metal hydride is added, preferably NaH. The mixture is maintained at about 15° to 35°, preferably 20 to 25 degrees for about 10 minutes to 2 hours, preferably 20 to 40 minutes. The appropriate halide, of formula $R^1X$ wherein X is chloro, bromo or iodo (in an amount slightly in excess of the compound of formula I but less than the metal hydride) is added and the reaction is carried out for about 10 minutes to 2 hours, preferably 20 to 40 minutes. The reaction mixture is then cooled, and the product isolated by conventional means.

The compounds of formula I as prepared in this manner may be isolated either as the hydrochloride salts or other salts or as the free base. Compounds isolated as a free base may optionally be converted into the corresponding salts; those isolated as salts may be converted into the free base form or into other salts by direct salt interchange.

In addition, compounds of the invention wherein $R^1$ is hydrogen may optionally be converted into those compounds wherein $R^1$ is alkyl or optionally substituted phenyl lower alkyl by treatment with a suitable alkyl or phenyl lower alkyl halide.

PREFERRED EMBODIMENTS

The preferred embodiments outlined hereinbelow are intended to include both the free base form and the pharmaceutically acceptable salts of the compounds enumerated.

Preferred compounds of the present invention are those wherein two of the R groups are hydrogen. Also preferred, are those compounds wherein $R^1$ is hydrogen, lower alkyl phenyl, or benzyl. More preferred among these are those compounds wherein at least one of the R groups is optionally substituted phenyl or optionally substituted phenyl lower alkyl. Another preferred group is that wherein all of the R groups are hydrogen, and especially preferred among these compounds are those wherein $R^1$ is hydrogen, lower alkyl phenyl, or benzyl. Most preferred are those compounds selected from the group consisting of:
4-phenyl-(1,4-benzodioxan-2-ylmethyl)imidazoline;
4-phenyl-(1,4-benzodioxan-2-yl)imidazoline;
1-phenyl-2-(1,4-benzodioxan-2-ylmethyl)imidazoline;
2-(1,4-benzodioxan-2-yl)imidazoline;
2-(1,4-benzodioxan-2-ylmethyl)imidazoline;
1-ethyl-2-(1,4-benzodioxan-2-ylmethyl)imidazoline.

UTILITY AND ADMINISTRATION

The compounds of the invention have been shown to effect $\alpha_2$ blockade in pithed rats and accordingly are useful in the affecting physiological phenomena controlled by $\alpha_2$ receptors. Among these phenomena are blood pressure, platelet aggregation, and mood. These compounds are, therefore, useful in treating hypertension and depression and in inhibiting platelet aggregation in human beings.

Administration of the active compounds and salts described herein can be via any of the accepted modes of administration for therapeutic agents which affect $\alpha_2$ receptors. These methods include oral, parenteral and otherwise systemic forms. The preferred method of administration is oral, except in those cases where the subject is unable to inject, by himself, any medication. In those instances it may be necessary to administer the composition intraveneously.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 0.1-10 mg/kg/day, preferably 0.5-5 mg/kg/day. For an average 70 kg human, this would amount to 7-700 mg per day, or preferably 35-350 mg/day.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%-95% active ingredient, preferably 25-70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The following examples serve to illustrate the invention. They should not be construed as narrowing it, or limiting its scope.

PREPARATION 1

Preparation of ethyl (1,4-benzodioxan-2-ylmethyl)acetimidate hydrochloride

A. 17.5 g (0.10 mole) 2-cyanomethyl-1,4-benzodioxane, prepared as described by Augstein, et al, *J. Med. Chem.* 8: 446 (1965), was dissolved in a mixture containing 7 g ethanol and 50 ml diethyl ether. 4.5 g (0.15 moles) of dry HCl was bubbled though the mixture, which was then capped. The mixture was allowed to stand at 5° C. for 4 days, followed by 3 days at room temperature. The crude product imidate hydrochloride (IV) precipitated out and was harvested by filtration, and washed with 100 ml ether, followed by 3×100 ml portions of methylene chloride. The solid was then purified by thin layer chromatography using 10% methanol in chloroform as a developing solvent. The product has an $R_f$ value of 0.7–0.8; starting material moves farther in this solvent system, and none was present in the crude product. The yield of product was 15.3 g, as the hydrochloride, or 59% yield.

B. In a manner similar to that outlined in Part A, but substituting for 2-cyanomethyl-1,4-benzodioxane,
2-cyano-1,4-benzodioxane,
2-(2-cyanoethyl)-1,4-benzodioxane,
2-(3-cyanopropyl)-1,4-benzodioxane,
the corresponding ethyl acid imidates may be prepared.

EXAMPLE 1

Conversion of Ethyl(1,4-benzodioxan-2-ylmethyl) acid imidate.HCl to 2-(1,4-benzodioxan-2-ylmethyl-4-phenyl-imidazoline hydrochloride A. 1-Phenylethylenediamine (6.85 g) and the imidate salt prepared in Preparation 1 (10 g) in 100 ml of ethanol were refluxed for 10 hours. The mixture was evaporated and the residue was dissolved in 5% aqueous hydrochloric acid and washed with ether. After neutralization with ammonium hydroxide, the aqueous layer was extracted with ether and the ether was dried and evaporated to afford 10 g of the free base as a foam. The hydrochloride salt was prepared by dissolving the base in methanolic-HCl and adding ether until crystallization occurred, m.p. 175°–176°.

B. Using the appropriate benzodioxanyl imidate derivative as prepared by Preparation 1, and following the procedure of Part A of this Example, the following compounds of the invention, as representative of the embodiments, herein may be prepared. The following list is illustrative, and is not intended to limit the invention:

1-phenyl-2-(1,4-benzodioxan-2-ylmethyl)imidazoline as the hydrochloride, m.p. 40°–42°;

2-(1,4-benzodioxan-2-yl)imidazoline as the hydrochloride, m.p. 195°–196°;

4-phenyl-2-(1,4-benzodioxan-2-yl)imidazoline as the hydrochloride, m.p. 185°–186°;

2-(1,4-benzodioxan-2-ylmethyl)imidazoline as the hydrochloride, m.p. 235°–236°;

1-ethyl-2-(1,4-benzodioxan-2-ylmethyl)imidazoline as the hydrochloride, m.p. 88°–90°;

1-n-propyl-2-[3-(1,4-benzodioxan-2-ylpropyl)-]imidazoline;

1-phenyl-2-[2-(1,4-benzodioxan-2-ylethyl)]-4-(2-chlorophenyl)imidazoline;

1-benzyl-2-(1,4-benzodioxan-2-ylmethyl)]-5-(3,4-dimethylphenyl)imidazoline;

2-[3-(1,4-benzodioxan-2-ylpropyl)]-4-(4-trifluoromethylbenzyl)imidazoline;

2-[2-(1,4-benzodioxan-2-ylethyl)]-5-[3-(2,4-dibromophenyl)-n-propyl)imidazoline.

EXAMPLE 2

Conversion of Free Base to Salt

Excess 3% hydrogen chloride in methanol is added to a solution of 1.0 g. 2-(1,4-benzodioxan-2-yl)imidazoline in 20 ml methanol. Diethyl ether is added until precipitation is complete. The product is filtered, washed with ether, air dried and recrystallized to give 2-(1,4-benzodioxan-2-yl)imidazoline.HCl.

In a similar manner, all compounds of Formula I in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 3

Conversion of Salt to Free Base 1.0 g of 2-(1,4-benzodioxan-2-yl)imidazoline.2HCl suspended in 50 ml of ether is stirred with excess dilute aqueous potassium carbonate solution until the salt is completely dissolved. The organic layer is then separated, washed twice with water, dried over magnesium sulfate and evaporated to yield 2-(1,4-benzodioxan-2-yl)imidazoline as the free base.

EXAMPLE 4

Directed interchange of acid addition salts 2-(1,4-benzodioxan-2-yl)imidazoline 2-(1,4-benzodioxan-2-yl)imidazoline acetate (1.0 g) is dissolved in a solution of 1 ml 50% aqueous sulfuric acid in 10 ml ethanol, and the solution evaporated to dryness. The product is suspended in ethanol and filtered, air dried and recrystallized from methanol/acetone to yield 2-(1,4-benzodioxan-2-yl)imidazoline: $HSO_4$.

In Examples 1 through 3, the active ingredient is 2-(1,4-benzodioxan-2-yl)imidazoline as the hydrochloride. Other compounds of Formula I and the pharmaceutically acceptable salts thereof may be substituted therein.

EXAMPLE 5

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 6

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 7

| Ingredients | Quantity per tablet, mgs. |
| --- | --- |
| Active ingredient | 1 |
| cornstarch | 50 |
| lactose | 145 |
| magnesium stearate | 5 |

The above ingredients are mixed intimately and pressed into single scored tablets.

EXAMPLE 8

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 9

| Ingredients | Quantity per tablet, mgs. |
| --- | --- |
| Active ingredient | 150 |
| lactose | 92 |

The above ingredients are mixed and introduced into a hard-shell gelatin capsule.

EXAMPLE 10

An injectable preparation buffered to a pH of 7 is prepared having the following composition:

| Ingredients | |
| --- | --- |
| Active ingredient | 0.2 g |
| KH$_2$PO$_4$ buffer (0.4 M solution) | 2 ml |
| KOH (1 N) | q.s. to pH 7 |
| water (distilled, sterile) | q.s. to 20 ml |

EXAMPLE 11

An oral suspension is prepared having the following composition:

| Ingredients | |
| --- | --- |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

We claim:
1. The compound 4-phenyl-2-(1,4-benzodioxan-2-ylmethyl)imidazoline or a pharmaceutically acceptable acid addition salt thereof.
2. The compound 4-phenyl-2-(1,4-benzodioxan-2-yl)imidazoline or a pharmaceutically acceptable acid addition salt thereof.
3. The compound 1-phenyl-2-(1,4-benzodioxan-2-ylmethyl)imidazoline or a pharmaceutically acceptable acid addition salt thereof.

* * * * *